(12) United States Patent
Hirotomi et al.

(10) Patent No.: US 10,349,659 B2
(45) Date of Patent: Jul. 16, 2019

(54) PLANT DISEASE CONTROL COMPOSITION AND PLANT DISEASE CONTROL METHOD

(71) Applicant: SUMITOMO CHEMICAL COMPANY, LIMITED, Tokyo (JP)

(72) Inventors: Dai Hirotomi, Kasai (JP); So Kiguchi, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/748,799

(22) PCT Filed: Aug. 10, 2016

(86) PCT No.: PCT/JP2016/073634
§ 371 (c)(1),
(2) Date: Jan. 30, 2018

(87) PCT Pub. No.: WO2017/026525
PCT Pub. Date: Feb. 16, 2017

(65) Prior Publication Data
US 2019/0008150 A1  Jan. 10, 2019

Related U.S. Application Data

(63) Continuation of application No. PCT/JP2016/073634, filed on Aug. 10, 2016.

(30) Foreign Application Priority Data

Aug. 11, 2015 (JP) .................. 2015-158974
Dec. 25, 2015 (JP) .................. 2015-253223

(51) Int. Cl.
*A01N 43/56* (2006.01)
*A01N 43/50* (2006.01)
*A01N 43/653* (2006.01)

(52) U.S. Cl.
CPC ............ *A01N 43/56* (2013.01); *A01N 43/50* (2013.01); *A01N 43/653* (2013.01)

(58) Field of Classification Search
None
See application file for complete search history.

(56) References Cited

U.S. PATENT DOCUMENTS

| 2013/0096174 A1 | 4/2013 | Matsuzaki et al. |
| 2014/0135213 A1 | 5/2014 | Mukumoto et al. |
| 2014/0179517 A1 | 6/2014 | Araki et al. |
| 2014/0315967 A1 | 10/2014 | Araki et al. |
| 2015/0181876 A1 | 7/2015 | Matsuzaki |
| 2016/0270398 A1 | 9/2016 | Miyake et al. |
| 2016/0295865 A1 | 10/2016 | Miyake et al. |
| 2016/0316753 A1 | 11/2016 | Miyake et al. |

FOREIGN PATENT DOCUMENTS

| JP | 2012-25735 A | 2/2012 |
| JP | 2014-19681 A | 2/2014 |
| JP | 2014-94920 A | 5/2014 |
| WO | WO 2011/070771 A1 | 6/2011 |
| WO | WO 2011/135833 A1 | 11/2011 |
| WO | WO 2011/162397 A1 | 12/2011 |

(Continued)

OTHER PUBLICATIONS

U.S. Appl. No. 15/748,732, filed Jan. 30, 2018.
(Continued)

*Primary Examiner* — Alton N Pryor
(74) *Attorney, Agent, or Firm* — Birch, Stewart, Kolasch & Birch, LLP

(57) ABSTRACT

The present invention provides a plant disease control composition that has excellent plant disease controlling effects and that contains a carboxamide compound represented by formula (1) and an azole compound represented by formula (2) [wherein $R^1$ represents a C1-6 alkyl group, $R^2$ represents a hydrogen atom or the like, A represents a nitrogen atom or the like, $Y^1$ represents a halogen atom, and n represents 0 or 1]. The present invention also provides a plant disease control method that includes a step for treating a plant or the soil in which a plant is being cultivated with an effective dose of the carboxamide compound represented by formula (1) and of the azole compound represented by formula (2).

7 Claims, No Drawings

(56) References Cited

FOREIGN PATENT DOCUMENTS

| WO | WO 2012/169516 A1 | 12/2012 |
|----|-------------------|---------|
| WO | WO 2013/077265 A1 | 5/2013  |
| WO | WO 2015-083436 A1 | 6/2015  |
| WO | WO 2015/083437 A1 | 6/2015  |
| WO | WO 2015/083438 A1 | 6/2015  |

OTHER PUBLICATIONS

U.S. Appl. No. 15/748,977, filed Jan. 30, 2018.
U.S. Appl. No. 15/748,739, filed Jan. 30, 2018.
English translation of the International Search Report (form PCT/ISA/210), dated Sep. 6, 2016, for International Application No. PCT/JP2016/073634.
International Preliminary Report on Patentability and English translation of the Written Opinion of the International Searching Authority (forms PCT/IB/373 and PCT/ISA/237), dated Feb. 13, 2018, for International Application No. PCT/JP2016/073634.
Extended European Search Report, dated Dec. 19, 2018, for European Application No. 16835222.7.

PLANT DISEASE CONTROL COMPOSITION AND PLANT DISEASE CONTROL METHOD

TECHNICAL FIELD

This application claims priority to and the benefit of Japanese Patent Application Nos. 2015-158974 filed on Aug. 11, 2015 and 2015-253223 filed on Dec. 25, 2015, the entire contents of which are incorporated herein by reference.

The present invention relates to a composition for controlling plant diseases and a method for controlling plant diseases.

BACKGROUND ART

Hitherto, some compounds have been known as active ingredient for a composition for controlling plant diseases (see Patent Documents 1 and 2).

CITATION LIST

Patent Document

Patent Document 1: WO 2011/162397 pamphlet
Patent Document 2: WO 2012/169516 pamphlet

SUMMARY OF THE INVENTION

Problems to be Solved by Invention

An object of the present invention is to provide a composition for controlling plant diseases and a method for controlling plant diseases, each having an excellent control efficacy on plant disease.

Means to Solve Problems

The present inventors have intensively studied to find out a composition for controlling plant diseases and a method for controlling plant diseases, each having an excellent control efficacy on plant diseases. As a result, they have found that a composition comprising a carboxamide compound represented by the below-mentioned formula (1) and an azole compound represented by the below-mentioned formula (2) shows an excellent control efficacy on plant diseases.

That is, the present invention provides the followings:

[1] A composition for controlling a plant disease comprising a carboxamide compound represented by a formula (1):

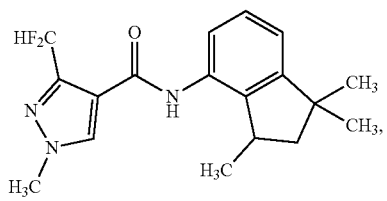

(1)

and an azole compound represented by a formula (2):

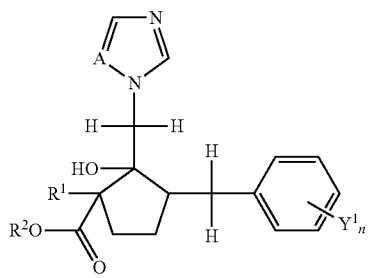

(2)

wherein
$R^1$ represents a C1-C6 alkyl group,
$R^2$ represents a hydrogen atom, a C1-C3 alkyl group, a C2-C3 alkenyl group, or a C2-C3 alkylnyl group,
A represents a nitrogen atom or a methine group,
$Y^1$ represents a halogen atom, and
n is 0 or 1.

[2] The composition for controlling a plant disease described in [1] wherein the compound represented by the formula (2) represents a compound represented by a formula (2a):

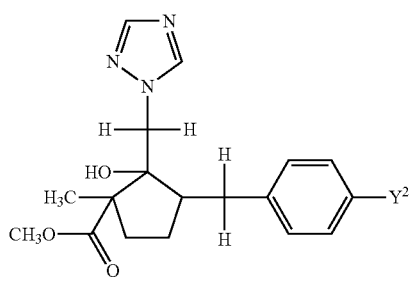

(2a)

wherein
$Y^2$ represents a chlorine atom, a fluorine atom or a hydrogen atom.

[3] The composition for controlling a plant disease described [2] wherein the compound represented by the formula (2a) is the compound wherein $Y^2$ represents a chlorine atom in the formula (2a).

[4] The composition for controlling a plant described in any one of [1] to [3] wherein a weight ratio of the compound represented by the formula (1) to the compound represented by the formula (2) is 1:0.0125 to 1:500.

[5] A method for controlling a plant disease comprising applying each of an effective amount of a carboxamide compound represented by a formula (1):

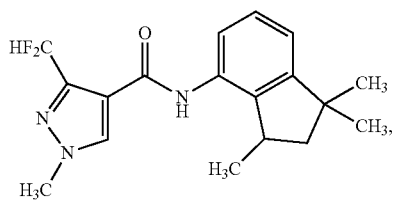

(1)

and an azole compound represented by a formula (2):

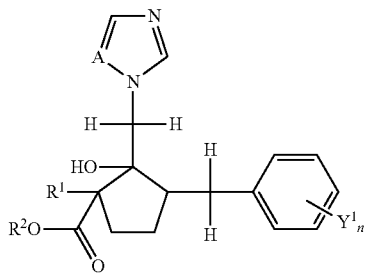

(2)

wherein
R¹ represents a C1-C6 alkyl group,
R² represents a hydrogen atom, a C1-C3 alkyl group, a C2-C3 alkenyl group, or a C2-C3 alkylnyl group,
A represents a nitrogen atom or a methine group,
Y¹ represents a halogen atom, and
n is 0 or 1,
to a plant or a soil for cultivating the plant.
[6] The method for controlling a plant disease described in [5] wherein the step of application to a plant or a soil for cultivating the plant is a step of application to a seed.
[7] A combined use of a carboxamide compound represented by a formula (1):

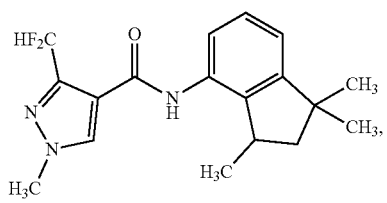

(1)

and an azole compound represented by a formula (2):

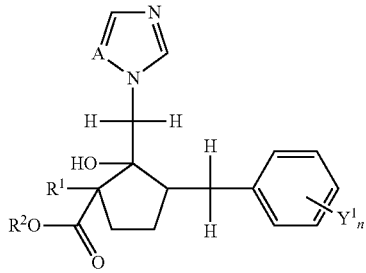

(2)

wherein
R¹ represents a C1-C6 alkyl group,
R² represents a hydrogen atom, a C1-C3 alkyl group, a C2-C3 alkenyl group, or a C2-C3 alkylnyl group,
A represents a nitrogen atom or a methine group,
Y¹ represents a halogen atom, and
n is 0 or 1.
The present invention can control plant diseases.

EMBODIMENT FOR CARRYING OUT THE INVENTION

The composition for controlling plant diseases of the present invention (hereinafter, referred to as "present com-position") comprises the above-mentioned carboxamide compound represented by the formula (1) (hereinafter, referred to as "present compound 1") and the above-mentioned azole compound represented by the formula (2) (hereinafter, referred to as "present compound 2").

The substituent(s) as described herein is/are explained.
The expression of "C1-C3" as described herein represents that the number of the carbon atom is from 1 to 3.
The term of "halogen atom" as described herein represents a fluorine atom, a chlorine atom, a bromine atom, and an iodine atom.
The term of "C1-C6 alkyl group" as described herein represents a straight- or branched-chain saturated hydrocarbon group having 1 to 6 of carbon atom(s), and includes, for example, a methyl group, an ethyl group, a propyl group, an isopropyl group, a butyl group, an isobutyl group, a sec-butyl group, a tert-butyl group, a pentyl group, a neopentyl group, a hexyl group, and the like. Also, the term of "C1-C3 alkyl group" as described herein represents a straight- or branched-saturated hydrocarbon group having 1 to 3 of carbon atom(s), and includes, for example, a methyl group, an ethyl group, a propyl group, and an isopropyl group.
The term of "C2-C3 alkenyl group" as described herein represents a straight- or branched-chain unsaturated hydrocarbon group having 2 to 3 of carbon atoms, and includes, for example, a vinyl group, a 1-propenyl group, an isopropenyl group, and a 2-propenyl group.
The term of "C2-C3 alkynyl group" as described herein represents a straight chain unsaturated hydrocarbon group having 2 to 3 of carbon atoms, and includes, for example, an ethynyl group, a 1-propynyl group, and a 2-propynyl group.

First, the present compound 1 is described.
The present compound 1 includes an enantiomer. Accordingly, the present compound 1 may include these enantiomers each singly, or any mixture composed of these enantiomers in each an arbitrary ratio of the respective enantiomers (for example, racemic mixture). Specific examples of enantiomer included in the present compound 1 are shown in Table 1.

TABLE 1

| Enantiomer | Structural formula |
|---|---|
| Present compound 1-R | |
| Present compound 1-S | |

The Present compound 1 is a compound described in, for example, WO 2011/162397 pamphlet, and may be prepared according to a process described therein.
Next, the present compound 2 is described.
In the above-mentioned formula (2), R¹ includes preferably a C1-C4 alkyl group, more preferably a methyl group or an ethyl group, and further preferably a methyl group.

In the above-mentioned formula (2), $R^2$ includes preferably a hydrogen atom, a methyl group, an ethyl group, or a propyl group, and more preferably a methyl group.

When n is 1, the binding position of $Y^1$ is not particularly limited, but is preferably the position that results in a 4-substituted benzyl group.

The present compound 2 is described, for example, in WO 2012/169516 pamphlet. The present compound 2 may be prepared according to a known process.

Examples of the present compound 2 include the following compounds.

A compound represented by the formula (2a):

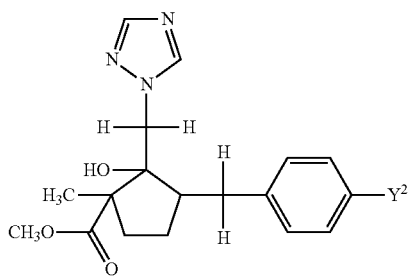

(2a)

wherein
$Y^2$ represents a chlorine atom, a fluorine atom, and a hydrogen atom.

A compound represented by the above-mentioned formula (2a) wherein $Y^2$ represents a chlorine atom (hereainfter, referred to as present compound 2-1);

A compound represented by the above-mentioned formula (2a) wherein $Y^2$ represents a fluorine atom (hereainfter, referred to as present compound 2-2); and A compound represented by the above-mentioned formula (2a) wherein $Y^2$ represents a hydrogen atom (hereainfter, referred to as present compound 2-3).

Here the present compound 2 includes an enantiomer and a diastereomer due to a configuration of organic residues that are bounded to a cyclopentane ring. Accordingly, the present compound 2 may include these isomers each singly, or any mixture composed of these isomers in each an arbitrary ratio of the respective isomers (for example, racemic mixture or diastereomeric mixture). Among them, the present compound 2 wherein a hydroxy group bounded to a cyclopentane ring and a —$R^1$ group are located in cis form to each other is preferred, and the present compound 2 wherein a hydroxy group bonded to a cyclopentane ring, a —$R^1$ group and a substituted or unsubstituted benzyl group are located in cis form to one another is more preferred.

Specific examples of optical active isomers that are included in the present compound 2 are shown in Tables 2 to 4.

TABLE 2

| Optical Active Isomer | Compound Name |
|---|---|
| Present compound 2-4 | Methyl (1R,2S,3S)-3-[(4-chlorophenyl)methyl]-2-hydroxy-1-methyl-2-(1H-1,2,4-triazol-1-ylmethyl)cyclopentane carboxylate |
| Present compound 2-5 | Methyl (1S,2R,3R)-3-[(4-chlorophenyl)methyl]-2-hydroxy-1-methyl-2-(1H-1,2,4-triazol-1-ylmethyl)cyclopentane carboxylate |

TABLE 2-continued

| Optical Active Isomer | Compound Name |
|---|---|
| Present compound 2-6 | Methyl (1R,2R,3R)-3-[(4-chlorophenyl)methyl]-2-hydroxy-1-methyl-2-(1H-1,2,4-triazol-1-ylmethyl)cyclopentane carboxylate |
| Present compound 2-7 | Methyl (1S,2S,3S)-3-[(4-chlorophenyl)methyl]-2-hydroxy-1-methyl-2-(1H-1,2,4-triazol-1-ylmethyl)cyclopentane carboxylate |
| Present compound 2-8 | Methyl (1R,2R,3S)-3-[(4-chlorophenyl)methyl]-2-hydroxy-1-methyl-2-(1H-1,2,4-triazol-1-ylmethyl)cyclopentane carboxylate |
| Present compound 2-9 | Methyl (1S,2S,3R)-3-[(4-chlorophenyl)methyl]-2-hydroxy-1-methyl-2-(1H-1,2,4-triazol-1-ylmethyl)cyclopentane carboxylate |
| Present compound 2-10 | Methyl (1R,2S,3R)-3-[(4-chlorophenyl)methyl]-2-hydroxy-1-methyl-2-(1H-1,2,4-triazol-1-ylmethyl)cyclopentane carboxylate |
| Present compound 2-11 | Methyl (1S,2R,3S)-3-[(4-chlorophenyl)methyl]-2-hydroxy-1-methyl-2-(1H-1,2,4-triazol-1-ylmethyl)cyclopentane carboxylate |

TABLE 3

| Optical active isomer | Compound Name |
|---|---|
| Present compound 2-12 | Methyl (1R,2S,3S)-3-[(4-fluorophenyl)methyl]-2-hydroxy-1-methyl-2-(1H-1,2,4-triazol-1-ylmethyl)cyclopentane carboxylate |
| Present compound 2-13 | Methyl (1S,2R,3R)-3-[(4-fluorophenyl)methyl]-2-hydroxy-1-methyl-2-(1H-1,2,4-triazol-1-ylmethyl)cyclopentane carboxylate |
| Present compound 2-14 | Methyl (1R,2R,3R)-3-[(4-fluorophenyl)methyl]-2-hydroxy-1-methyl-2-(1H-1,2,4-triazol-1-ylmethyl)cyclopentane carboxylate |
| Present compound 2-15 | Methyl (1S,2S,3S)-3-[(4-fluorophenyl)methyl]-2-hydroxy-1-methyl-2-(1H-1,2,4-triazol-1-ylmethyl)cyclopentane carboxylate |
| Present compound 2-16 | Methyl (1R,2R,3S)-3-[(4-fluorophenyl)methyl]-2-hydroxy-1-methyl-2-(1H-1,2,4-triazol-1-ylmethyl)cyclopentane carboxylate |
| Present compound 2-17 | Methyl (1S,2S,3R)-3-[(4-fluorophenyl)methyl]-2-hydroxy-1-methyl-2-(1H-1,2,4-triazol-1-ylmethyl)cyclopentane carboxylate |
| Present compound 2-18 | Methyl (1R,2S,3R)-3-[(4-fluorophenyl)methyl]-2-hydroxy-1-methyl-2-(1H-1,2,4-triazol-1-ylmethyl)cyclopentane carboxylate |
| Present compound 2-19 | Methyl (1S,2R,3S)-3-[(4-fluorophenyl)methyl]-2-hydroxy-1-methyl-2-(1H-1,2,4-triazol-1-ylmethyl)cyclopentane carboxylate |

TABLE 4

| Optical active isomer | Compound Name |
|---|---|
| Present compound 2-20 | Methyl (1R,2S,3S)-3-phenylmethyl-2-hydroxy-1-methyl-2-(1H-1,2,4-triazol-1-ylmethyl)cyclopentane carboxylate |

TABLE 4-continued

| Optical active isomer | Compound Name |
|---|---|
| Present compound 2-21 | Methyl (1S,2R,3R)-3-phenylmethyl-2-hydroxy-1-methyl-2-(1H-1,2,4-triazol-1-ylmethyl)cyclopentane carboxylate |
| Present compound 2-22 | Methyl (1R,2R,3R)-3-phenylmethyl-2-hydroxy-1-methyl-2-(1H-1,2,4-triazol-1-ylmethyl)cyclopentane carboxylate |
| Present compound 2-23 | Methyl (1S,2S,3S)-3-phenylmethyl-2-hydroxy-1-methyl-2-(1H-1,2,4-triazol-1-ylmethyl)cyclopentane carboxylate |
| Present compound 2-24 | Methyl (1R,2R,3S)-3-phenylmethyl-2-hydroxy-1-methyl-2-(1H-1,2,4-triazol-1-ylmethyl)cyclopentane carboxylate |
| Present compound 2-25 | Methyl (1S,2S,3R)-3-phenylmethyl-2-hydroxy-1-methyl-2-(1H-1,2,4-triazol-1-ylmethyl)cyclopentane carboxylate |
| Present compound 2-26 | Methyl (1R,2S,3R)-3-phenylmethyl-2-hydroxy-1-methyl-2-(1H-1,2,4-triazol-1-ylmethyl)cyclopentane carboxylate |
| Present compound 2-27 | Methyl (1S,2R,3S)-3-phenylmethyl-2-hydroxy-1-methyl-2-(1H-1,2,4-triazol-1-ylmethyl)cyclopentane carboxylate |

The weight ratio of the present compound 1 to the present compound 2 in the present composition is usually 1:0.0125 to 1:500, preferably 1:0.025 to 1:100, and more preferably 1:0.1 to 1:10.

Although the present composition may be a mixture as itself of the present compound 1 and the present compound 2, the present composition is usually prepared by mixing the present compound 1, the present compound 2, and an inert carrier, and if necessary, adding a surfactant or other pharmaceutical additives, and then formulating into the form of oil solution, emulsifiable concentrate, flowable formulation, wettable powder, granulated wettable powder, dust formulation, granules and so on. Such formulations can be used by itself or with an addition of other inert components as an agent for controlling a plant disease.

The present composition may contain usually 0.1 to 99% by weight, preferably 0.2 to 90% by weight, and more preferably 1 to 80% by weight of the present compound 1 and the present compound 2 in total.

Examples of an inert carrier used on the formulation include a solid carrier and a liquid carrier, and examples of the solid carrier include finely-divided powders or particles consisting of minerals (for example, kaolin clay, attapulgite clay, bentonite, montmorillonite, acid clay, pyrophyllite, talc, diatomaceous earth, or calcite), natural organic substances (for example, corncob powder, or walnut shell powder), synthetic organic substances (for example, urea), salts (for example, calcium carbonate, or ammonium sulfate), synthetic inorganic substances (for example, synthetic hydrous silicon oxide) and so on. Examples of the liquid carrier include aromatic hydrocarbons (for example, xylene, alkyl benzene, or methylnaphthalene), alcohols (for example, 2-propanol, ethylene glycol, propylene glycol, or ethylene glycol monoethyl ether), ketones (for example, acetone, cyclohexanone, or isophorone), vegetable oils (for example, soybean oil, or cotton oils), petroleum-derived aliphatic hydrocarbons, esters, dimethyl sulfoxide, acetonitrile and water.

Examples of the surfactant include anionic surfactant (for example, alkyl sulfate salts, alkylaryl sulfonate salts, dialkyl sulfosuccinate salts, polyoxyethylene alkylaryl ether phosphates, lignin sulfonate, or naphthalenesulfonate formaldehyde polycondensation), nonionic surfactant (for example, polyoxyethylene alkylaryl ether, polyoxyethylene alkyl polyoxypropylene block copolymer, or sorbitan fatty acid ester) and cationic surfactant (for example, alkyltrimethyl ammonium salts).

Examples of the other pharmaceutical additives include water-soluble polymer (for example, polyvinyl alcohol, or polyvinyl pyrrolidone), polysaccharides (for example, arabic gum, alginic acid and salts thereof, CMC (carboxymethyl-cellulose), or xanthan gum), inorganic substances (for example, aluminum magnesium silicate, or alumina-sol), antiseptic agent, coloring agent, and PAP (isopropyl acid phosphate), and stabilizing agent (for example, BHT (2,6-di-tert-butyl-4-methylphenol)).

The present composition can also be prepared by separately formulating the present compound 1 and the present compound 2 into different formulations according to the above-mentioned procedures, if necessary, further diluting each of them with water, thereafter, mixing the separately prepared different formulations comprising the present compound 1 or the present compound 2, respectively, or the dilute solutions thereof with each other.

The present composition may further comprise one or more other fungicide(s) and/or insecticide(s).

The present composition can be applied to a plant or a soil for cultivating the plant to control the plant diseases.

Examples of the plant diseases which can be controlled by the present invention include plant diseases which are caused by a plant pathogenic filamentous fungus or other pathogens mediated by the plant pathogenic filamentous fungus, but are not limited thereto.

Rice diseases: blast (*Magnaporthe grisea*), brown spot (*Cochliobolus miyabeanus*), sheath blight (*Rhizoctonia solani*), and bakanae disease (*Gibberella fujikuroi*);

Wheat diseases: powdery mildew (*Erysiphe graminis*), fusarium blight (*Fusarium graminearum, F. avenaceum, F. culmorum, Microdochium nivale*), rust (for example, yellow rust (*Puccinia striiformis*), black rust (*P. graminis*), red rust (*P. recondita*)), snow mould (*Micronectriella nivale*), typhula snow blight (*Typhula* sp.), loose smut (*Ustilago tritici*), stinking smut (*Tilletia caries*), eyespot (*Pseudocercosporella herpotrichoides*), leaf blotch (*Mycosphaerella graminicola*), glume blotch (*Stagonospora nodorum*), and tan spot (*Pyrenophora tritici-repentis*);

Barley diseases: powdery mildew (*Erysiphe graminis*), loose smut (*Fusarium graminearum, F. avenaceum, F. culmorum, Microdochium nivale*), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), and damping-off caused by *rhizoctonia* fungus (*Rhizoctonia solani*);

Corn diseases: smut (*Ustilago maydis*), southern leaf blight (*Cochliobolus heterostrophus*), zonate leaf spot (*Gloeocercospora sorghi*), southern rust (*Puccinia polysora*), gray leaf spot (*Cercospora zeae-maydis*), and damping-off caused by *rhizoctonia* fungus (*Rhizoctonia solani*);

Citrus diseases: melanose (*Diaporthe citri*), scab (*Elsinoe fawcetti*), fruit rot (*Penicillium digitatum, P. italicum*), and *Phytophthora* disease (*Phytophthora parasitica, Phytophthora citrophthora*);

Apple diseases: blossom blight (*Monilinia mali*), canker (*Valsa ceratosperma*), powdery mildew (*Podosphaera leucotricha*), *Alternaria* leaf spot (*Alternaria alternata* apple pathotype), scab (*Venturia inaequalis*), bitter rot (*Colletotrichum acutatum*), and crown rot (*Phytophtora cactorum*);

Pear diseases: scab (*Venturia nashicola, V. pirina*), black spot (*Alternaria alternata* Japanese pear pathotype), rust (*Gymnosporangium haraeanum*), and *Phytophthora* crown and root rot (*Phytophthora cactorum*);

Peach diseases: brown rot (*Monilinia fructicola*), scab (*Cladosporium carpophilum*), and *Phomopsis* rot (*Phomopsis* sp.);

Grapes diseases: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), and downy mildew (*Plasmopara viticola*);

Diseases of Japanese persimmon: anthracnose (*Gloeosporium kaki*), and leaf spot (*Cercospora kaki*, *Mycosphaerella nawae*);

Diseases of Cucurbitaceae: anthracnose (*Colletotrichum lagenarium*), powdery mildew (*Sphaerotheca fuliginea*), gummy stem blight (*Mycosphaerella melonis*), Fusarium wilt (*Fusarium oxysporum*), downy mildew (*Pseudoperonospora cubensis*), *Phytophthora* rot (*Phytophthora* sp.), and damping-off (*Pythium* sp.);

Tomato diseases: early blight (*Alternaria solani*), leaf mold (*Cladosporium fulvum*), and late blight (*Phytophthora infestans*);

Eggplant disease: brown spot (*Phomopsis vexans*), and powdery mildew (*Erysiphe cichoracearum*);

Diseases of *brassica* family: *Alternaria* leaf spot (*Alternaria japonica*), white spot (*Cercosporella brassicae*), clubroot (*Plasmodiophora brassicae*), and downy mildew (*Peronospora parasitica*);

welsh onion diseases: rust (*Puccinia allii*), and downy mildew (*Peronospora destructor*);

Soybean diseases: purple stain (*Cercospora kikuchii*), *Sphaceloma* scad (*Elsinoe glycines*), pod and stem blight (*Diaporthe phaseolorum* var. *sojae*), septoria brown spot (*Septoria glycines*), *Cercospora* leaf spot (*Cercospora sojina*), rust (*Phakopsora pachyrhizi*), phytophthora root and stem rot (*Phytophthora sojae*), damping-off caused by *rhizoctonia* fungus (*Rhizoctonia solani*), target spot (*Corynespora casiicola*), and sclerotinia rot (*Sclerotinia sclerotiorum*);

Kidney bean diseases: anthracnose (*Colletotrichum lindemthianum*);

Peanut diseases: leaf spot (*Cercospora personata*), brown leaf spot (*Cercospora arachidicola*), and southern blight (*Sclerotium rolfsii*);

Garden pea diseases: powdery mildew (*Erysiphe pisi*);

Potato diseases: early blight (*Alternaria solani*), late blight (*Phytophthora infestans*), pink rot (*Phytophthora erythroseptica*), and powdery scab (*Spongospora subterranean* f. sp. *subterranea*);

Strawberry diseases: powdery mildew (*Sphaerotheca humuli*), and anthracnose (*Glomerella cingulata*);

Tea diseases: net blister blight (*Exobasidium reticulatum*), white scab (*Elsinoe leucospila*), gray blight (*Pestalotiopsis* sp.), and anthracnose (*Colletotrichum theae-sinensis*);

Tabacco diseases: brown spot (*Alternaria longipes*), powdery mildew (*Erysiphe cichoracearum*), anthracnose (*Colletotrichum tabacum*), downy mildew (*Peronospora tabacina*), and black shank (*Phytophthora nicotianae*);

Rape seed diseases: sclerotinia rot (*Sclerotinia sclerotiorum*), and rape seed damping-off caused by *Rhizoctonia solani* (*Rhizoctonia solani*);

Cotton diseases: cotton damping-off caused by *Rhizoctonia solani* (*Rhizoctonia solani*);

Sugar beet diseases: cercospora leaf spot (*Cercospora beticola*), leaf blight (*Thanatephorus cucumeris*), root rot (*Thanatephorus cucumeris*), and aphanomyces root rot (*Aphanomyces cochlioides*);

Rose diseases: blackspot (*Diplocarpon rosae*), powdery mildew (*Sphaerotheca pannosa*), and downy mildew (*Peronospora sparsa*);

Chrysanthemum and Asteraceae vegetable diseases: downy mildew (*Bremia lactucae*), leaf blight (*Septoria chrysanthemi-indici*), and rust (*Puccinia horiana*);

Various plants diseases: diseases caused by *Pythium* spp. (*Pythium aphanidermatum*, *Pythium debarianum*, *Pythium graminicola*, *Pythium irregulare*, *Pythium ultimum*), Gray mold (*Botrytis cinerea*), and *Sclerotinia* rot (*Sclerotinia sclerotiorum*);

Japanese radish diseases: *Alternaria* leaf spot (*Alternaria brassicicola*);

Turfgrass diseases: dollar spot (*Sclerotinia homeocarpa*), brown patch, and large patch (*Rhizoctonia solani*);

Banana diseases: Sigatoka disease (*Mycosphaerella fijiensis*, *Mycosphaerella musicola*);

Sunflower diseases: downy mildew (*Plasmopara halstedii*);

Seed diseases or diseases in the early stages of the growth of various plants caused by bacteria of *Aspergillus* spp., *Penicillium* spp., *Fusarium* spp., *Gibberella* spp., *Tricoderma* spp., *Thielaviopsis* spp., *Rhizopus* spp., *Mucor* spp., *Corticium* spp., *Phoma* spp., *Rhizoctonia* spp., *Diplodia* spp.; and Viral diseases of various plants mediated by *Polymixa* genus or *Olpidium* genus.

Examples of the plants to which the present composition can be applied include the followings, but are not limited thereto.

Crops: corn, rice, wheat, barley, rye, oat, sorghum, cotton, soybean, peanut, buckwheat, beet, rapeseed, sunflower, sugar cane, and tobacco, etc.;

Vegetables: solanaceous vegetables (eggplant, tomato, pimento, pepper, and potato, etc.), cucurbitaceous vegetables (cucumber, pumpkin, zucchini, water melon, melon, and squash, etc.), cruciferous vegetables (Japanese radish, white turnip, horseradish, kohlrabi, Chinese cabbage, cabbage, leaf mustard, broccoli, and cauliflower, etc.), asteraceous vegetables (burdock, crown daisy, artichoke, and lettuce, etc.), liliaceous vegetables (welsh onion, onion, garlic, and asparagus), ammiaceous vegetables (carrot, parsley, celery, and parsnip, etc.), chenopodiaceous vegetables (spinach, and Swiss chard, etc.), lamiaceous vegetables (perilla, mint, and basil, etc.), strawberry, sweet potato, glutinous yam, and eddoe, etc.;

Flowers;

Foliage plants;

Turfgrass;

Fruits: pomaceous fruits (apple, pear, Japanese pear, Chinese quince, and quince, etc.), stone fleshy fruits (peach, plum, nectarine, Japanese apricot (*Prunus mume*), cherry fruit, apricot, and prune, etc.), citrus fruits (Citrus unshiu, orange, lemon, lime, and grapefruit, etc.) nuts (chestnuts, walnuts, hazelnuts, almond, pistachio, cashew nuts, and macadamia nuts, etc.), berry fruits (blueberry, cranberry, blackberry, and raspberry, etc.), grapes, Japanese persimmon, olive, Japanese plum, banana, coffee, date palm, and coconuts, etc.; and Trees other than fruit trees: tea, mulberry, flowering plants, roadside trees (ash, birch, dogwood, eucalyptus, ginkgo (*ginkgo biloba*), lilac, maple, oak (*quercus*), poplar, Judas tree, Formosan gum (*Liquidambar formosana*), plane tree, *zelkova*, Japanese arborvitae (*Thuja standishii*), fir wood, hemlock, juniper, *pinus*, *picea*, and yew (*Taxus cuspidate*)), etc.

The aforementioned "plant(s)" may include plants which resistance has been imparted by genetic recombination.

Exemplary embodiments of the present composition include the followings, but are not limited thereto.

A present composition wherein the combination of the present compound 1 and the present compound 2 represents as follows:

a combination of the present compound 1 and the present compound 2-1;
a combination of the present compound 1 and the present compound 2-2:
a combination of the present compound 1 and the present compound 2-3;
a combination of the present compound 1 and the present compound 2-4;
a combination of the present compound 1 and the present compound 2-5;
a combination of the present compound 1 and the present compound 2-6;
a combination of the present compound 1 and the present compound 2-7;
a combination of the present compound 1 and the present compound 2-8;
a combination of the present compound 1 and the present compound 2-9;
a combination of the present compound 1 and the present compound 2-10;
a combination of the present compound 1 and the present compound 2-11;
a combination of the present compound 1 and the present compound 2-12;
a combination of the present compound 1 and the present compound 2-13;
a combination of the present compound 1 and the present compound 2-14;
a combination of the present compound 1 and the present compound 2-15;
a combination of the present compound 1 and the present compound 2-16;
a combination of the present compound 1 and the present compound 2-17;
a combination of the present compound 1 and the present compound 2-18;
a combination of the present compound 1 and the present compound 2-19;
a combination of the present compound 1 and the present compound 2-20;
a combination of the present compound 1 and the present compound 2-21;
a combination of the present compound 1 and the present compound 2-22;
a combination of the present compound 1 and the present compound 2-23;
a combination of the present compound 1 and the present compound 2-24;
a combination of the present compound 1 and the present compound 2-25;
a combination of the present compound 1 and the present compound 2-26;
a combination of the present compound 1 and the present compound 2-27;
a combination of the present compound 1-R and the present compound 2-1;
a combination of the present compound 1-R and the present compound 2-2:
a combination of the present compound 1-R and the present compound 2-3;
a combination of the present compound 1-R and the present compound 2-4;
a combination of the present compound 1-R and the present compound 2-5;
a combination of the present compound 1-R and the present compound 2-6;
a combination of the present compound 1-R and the present compound 2-7;
a combination of the present compound 1-R and the present compound 2-8;
a combination of the present compound 1-R and the present compound 2-9;
a combination of the present compound 1-R and the present compound 2-10;
a combination of the present compound 1-R and the present compound 2-11;
a combination of the present compound 1-R and the present compound 2-12;
a combination of the present compound 1-R and the present compound 2-13;
a combination of the present compound 1-R and the present compound 2-14;
a combination of the present compound 1-R and the present compound 2-15;
a combination of the present compound 1-R and the present compound 2-16;
a combination of the present compound 1-R and the present compound 2-17;
a combination of the present compound 1-R and the present compound 2-18;
a combination of the present compound 1-R and the present compound 2-19;
a combination of the present compound 1-R and the present compound 2-20;
a combination of the present compound 1-R and the present compound 2-21;
a combination of the present compound 1-R and the present compound 2-22;
a combination of the present compound 1-R and the present compound 2-23;
a combination of the present compound 1-R and the present compound 2-24;
a combination of the present compound 1-R and the present compound 2-25;
a combination of the present compound 1-R and the present compound 2-26;
a combination of the present compound 1-R and the present compound 2-27.

A present composition comprising the present compound 1 and any one of the present compounds 2-1 to 2-27 wherein a weight ratio of the present compound 1 to any one of the present compounds 2-1 to 2-27 is 1:0.0125 to 1:500;

A present composition comprising the present compound 1 and any one of the present compounds 2-1 to 2-27 wherein a weight ratio of the present compound 1 to any one of the present compounds 2-1 to 2-27 is 1:0.025 to 1:100;

A present composition comprising the present compound 1 and any one of the present compounds 2-1 to 2-27 wherein a weight ratio of the present compound 1 to any one of the present compounds 2-1 to 2-27 is 1:0.1 to 1:10;

A present composition comprising the present compound 1-R and any one of the present compounds 2-1 to 2-27 wherein a weight ratio of the present compound 1-R to any one of the present compounds 2-1 to 2-27 is 1:0.0125 to 1:500;

A present composition comprising the present compound 1-R and any one of the present compounds 2-1 to 2-27 wherein a weight ratio of the present compound 1-R to any one of the present compounds 2-1 to 2-27 is 1:0.025 to 1:100;

A present composition comprising the present compound 1-R and any one of the present compounds 2-1 to 2-27 wherein a weight ratio of the present compound 1-R to any one of the present compounds 2-1 to 2-27 is 1:0.1 to 1:10.

The method for controlling plant diseases of the present invention (hereinafter, referred to as "control method of the present invention") is carried out by applying each of an effective amount of the present compound 1 and the present compound 2, to a plant or soil for cultivating the plant. Examples of the plant include foliage of a plant, seeds of a plant and bulbs of a plant. Moreover, the bulbs described herein mean discoid stems, corms, rhizomes, tubers, tuberous, and tuberous roots.

In the control method of the present invention, the present compound 1 and the present compound 2 may be applied separately to a plant or soil for cultivating the plant in the same period, but are usually applied as the present composition in terms of a convenience on applying.

In the control method of the present invention, examples of the method of applying the present compound 1 and the present compound 2 include foliage treatment, soil treatment, root treatment, and seed treatment.

Such the foliage treatment includes, for example, a method of applying the present compound 1 and the present compound 2 onto surface of a plant to be cultivated by a foliar application or a stem application.

Such the soil treatment includes, for example, soil broadcast, soil incorporation, and irrigation of the agent solution to a soil.

Such the root treatment includes, for example, a method of soaking a whole or a root of the plant into a medicinal solution comprising the present compound 1 and the present compound 2, and a method of attaching a solid formulation comprising the present compound 1, the present compound 2 and the solid carrier to a root of the plant.

Such the seed treatment includes, for example, an applying of the present composition to a seed or a bulb of the plant to be prevented from the plant disease, specifically, for example, spray treatment by spraying a suspension of the present composition in a mist form onto a surface of a seed or a surface of a bulb, smear treatment by applying the wettable powder, the emulsifiable concentrate or the flowable formulation of the present composition with added by small amounts of water or as itself to a seed or a bulb, immersion treatment by immersing a seed into a solution of the present composition for a certain period of time, film-coating treatment and pellet-coating treatment.

Each dose of the present compound 1 and the present compound 2 in the control method of the present invention may be varied depending on a kind of plant to be treated, a kind or a frequency of an occurrence of a plant disease as a control subject, a dosage form, a treatment period, a treatment method, a treatment site, a climate condition, etc. In case of an application to a foliage of the plant or a soil for cultivating the plant, a total amount of the present compound 1 and the present compound 2 is usually 1 to 500 g, preferably 2 to 200 g, and more preferably 10 to 100 g, per 1000 m². Also each dose of the present compound 1 and the present compound 2 in the treatment for seed is usually 0.001 to 10 g, and preferably 0.01 to 1 g, per 1 kg of seeds.

The emulsifiable concentrate, the wettable powder or the flowable formulation, etc., is usually applied by diluting them with water, and then spreading them. In this case, usually, each concentration of the present compound 1 and the present compound 2 contain 0.0005 to 2% by weight, and preferably 0.005 to 1% by weight of the present compound 1 and the present compound 2 in total. The dust formulation or the granular formulation, etc., is usually applied as itself without diluting them.

EXAMPLES

The present invention is described in more detail below by Formulation Examples and Test Examples, but the present invention should not be limited thereto.

First, Formulation Examples are described. Herein, "parts" means "parts by weight".

Formulation Example 1

Five (5) parts of the present compound 1, 5 parts of any one of the present compounds 2-1 to 2-27, 35 parts of a mixture of white carbon and polyoxyethylene alkylether sulfate ammonium salt (weight ratio 1:1), and 55 parts of water are mixed, and the resultant solution is then subjected to fine grinding according to a wet grinding method to obtain each flowable formulation.

Formulation Example 2

Five (5) parts of the present compound 1-R, 5 parts of any one of the present compounds 2-1 to 2-27, 35 parts of a mixture of white carbon and polyoxyethylene alkylether sulfate ammonium salt (weight ratio 1:1), and 55 parts of water are mixed, and the resultant solution is then subjected to fine grinding according to a wet grinding method to obtain each flowable formulation.

Formulation Example 3

Ten (10) parts of the present compound 1, 5 parts of any one of the present compounds 2-1 to 2-27, 1.5 parts of sorbitan trioleate, and 28 parts of aqueous solution that contained 2 parts of polyvinyl alcohol are mixed, and the resultant solution is then subjected to wet fine grinding method, and thereto are added 45.50 parts of an aqueous solution that contained 0.05 parts of xanthan gum and 0.1 part of aluminum magnesium silicate, followed by adding 10 parts of propylene glycol, and the mixture is blended by stirring to obtain each flowable formulation.

Formulation Example 4

Ten (10) parts of the present compound 1-R, 5 parts of any one of the present compounds 2-1 to 2-27, 1.5 parts of sorbitan trioleate, and 28 parts of aqueous solution that contained 2 parts of polyvinyl alcohol are mixed, and the resultant solution is then subjected to wet fine grinding method, and thereto are added 45.50 parts of an aqueous solution that contained 0.05 parts of xanthan gum and 0.1 part of aluminum magnesium silicate, followed by adding 10 parts of propylene glycol, and the mixture is blended by stirring to obtain each flowable formulation.

Formulation Example 5

Five (10) parts of the present compound 1, 40 parts of any one of the present compounds 2-1 to 2-27, 3 parts of calcium lignosulfonate, 2 parts of sodium lauryl sulfate and 45 parts of synthetic hydrous silicon oxide are fully ground and mixed to obtain each wettable powder.

Formulation Example 6

Five (10) parts of the present compound 1-R, 40 parts of any one of the present compounds 2-1 to 2-27, 3 parts of calcium lignosulfonate, 2 parts of sodium lauryl sulfate and 45 parts of synthetic hydrous silicon oxide are fully ground and mixed to obtain each wettable powder.

Formulation Example 7

Five (5) parts of the present compound 1, 5 parts of any one of the present compounds 2-1 to 2-27, 14 parts of polyoxyethylene styryl phenyl ether, 6 parts of dodecylbenzene sulfonic acid calcium salt, and 70 parts of xylene are mixed finely to obtain each formulation.

Formulation Example 8

Five (5) parts of the present compound 1-R, 5 parts of any one of the present compounds 2-1 to 2-27, 14 parts of polyoxyethylene styryl phenyl ether, 6 parts of dodecylbenzene sulfonic acid calcium salt, and 70 parts of xylene are mixed finely to obtain each formulation.

Next, Test Examples are described.

Test Example 1

The present compound 1, and any one of the present compounds 2-1 to 2-27 are mixed, and each of the resultant mixtures is diluted with dimethyl sulfoxide such that each concentration of the present compound 1 and the present compound 2 is 10 ppm. The resultant diluted solution is dispensed into a microtiter plate (with 96 wells) in 1 µl portion thereof. Thereto is then dispensed 150 µl of a potato dextrose broth medium (PDB medium) to which conidia of wheat leaf blight fungus (*Mycosphaerella graminicola*) is inoculated in advance. This plate is cultured at 18° C. for four days, thereby allowing wheat leaf blight fungus to undergo proliferation, and the absorbance at 550 nm of each well of the microtiter plate is then measured to examine a degree of growth of the wheat leaf blight fungus.

The efficacy is calculated on the basis of the obtained degree of growth of the treated group and the untreated group, respectively, by the below-mentioned "Equation 1". From the test results, a high efficacy is acknowledged.

$$\text{Efficacy} = 100 \times (X-Y)/X \quad \text{Equation 1}$$

X: Degree of growth of fungus in the untreated group
Y: Degree of growth of fungus in the treated group Test Example 2

A plastic pot is filled with soil and thereto wheat (cultivar. Shirogane) is seeded and the plants are grown in a greenhouse for ten days. Each of the present compound 1 and any one of the present compounds 2-1 to 2-27 is made to a formulation according to any of the above-mentioned Formulation Examples 1 to 8, and each of the resultant formulation is diluted with water such that each concentration of the present compound 1 and the present compound 2 respectively is 100 ppm. The resultant diluted solution is sprayed to foliar parts so as to adhere adequately onto the surfaces of leaves of the above wheats. After spraying the dilutions, the plants are air-dried and thereto an aqueous suspension of spores of wheat rust fungi (*Puccinia recondita*) is inoculated by spraying one day after the application. After the inoculation, the plants are placed at 27° C. under humid condition for one day, and are then cultivated under lighting for ten to fifteen days, and a lesion area is examined (hereinafter referred to as "treated group").

Whereas, wheats are cultivated similarly to the treated group except that no foliage application of the above-mentioned agent solutions are done (hereinafter referred to as "untreated group"). A lesion area of wheat rust fungi is examined similarly to the above-mentioned treated group.

From each of the lesion area of the treated group and the untreated group, the efficacy of the treated group is calculated by the following Equation 2. From the test results, a high efficacy is acknowledged.

$$\text{Efficacy} = [1-(\text{lesion area of the treated group})/(\text{lesion area of the untreated group})] \times 100 \quad \text{Equation 2}$$

Test Example 3

The present compound 1 or the present compound 2-1 was dissolved into dimethyl sulfoxide such that each concentration of the present compound 1 or the present compound 2-1 was adjusted to one hundred fifty times as much as the concentration indicated in the below-mentioned Table 5. The resultant agent solution was dispensed into a microtiter plate (with 96 wells) in 1 µl portion thereof per well. One hundred forty nine (149) µl of YBG medium (which was prepared by dissolving 10 g of yeast extract, 10 g of Bacto Peptone, and 20 mL of glycerol into 1 L of water, followed by sterilizing the medium) was dispensed into the wells to which the agent solution(s) was/were dispensed. The plate was cultivated at 18° C. for six days, thereby allowing wheat leaf blight fungus to undergo proliferation, and the absorbance at 550 nm of each well of the micro titer plate was then measured to examine a degree of growth of the wheat leaf blight fungus (hereinafter referred to as "treated group").

Whereas, wheat leaf blight fungus was proliferated similarly to the case of the treated group except that dimethyl sulfoxide was used instead of the agent solution, and the degree of the growth was examined (hereinafter referred to as "untreated group"). The efficacy was calculated from the respective obtained degree of growth by the below-mentioned "Equation 1".

From the test results, it was acknowledged that a synergistic effect was shown in the mixed-use group of the present compound 1 and the present compound 2-1 when compared with the single-use group of each of the above-mentioned compounds.

$$\text{Efficacy (\%)} = 100 \times (X-Y)/X \quad \text{Equation 1}$$

X: Degree of growth of fungus in the untreated group
Y: Degree of growth of fungus in the treated group

TABLE 5

| Testing compound | Concentration in medium (ppm) | mixing ratio (Present compound 1:Present compound 2-1) | Efficacy (%) |
|---|---|---|---|
| Present compound 1 | 0.1 | — | 70 |
| Present compound 1 | 0.005 | — | 15 |
| Present compound 2-1 | 0.05 | — | 69 |

TABLE 5-continued

| Testing compound | Concentration in medium (ppm) | mixing ratio (Present compound 1:Present compound 2-1) | Efficacy (%) |
|---|---|---|---|
| Present compound 2-1 | 0.01 | — | 27 |
| Present compound 1 + Present compound 2-1 | 0.1 + 0.01 | 1:0.1 | 100 |
| Present compound 1 + Present compound 2-1 | 0.005 + 0.05 | 1:10 | 100 |

Test Example 4

Five (5) parts of the present compound 1, 35 parts of a mixture of white carbon and ammonium polyoxyethylene alkyl ether sulfate (the weight ratio of 1:1) and 55 parts of water were mixed, and the mixture was then finely-ground by a wet grinding method to obtain a flowable formulation comprising the present compound 1. Separately, the flowable formulation comprising the present compound 2-1 was prepared according to the above-mentioned similar method except that the present compound 2-1 was used instead of the present compound 1 to form a flowable formulation comprising the present compound 2-1.

Each of the above-mentioned respective flowable formulations, and the flowable formulation comprising the present compound 1 and the present compound 2-1 that was prepared according to the above-mentioned Formulation Example 3 was diluted with water such that each concentration of the respective compounds in the dilution solutions was adjusted to that indicated in Table 6, to prepare the dilution solutions, respectively.

A plastic pot was filled with soil, and thereto wheat (cultivar. Shirogane) was seeded, and the plants were grown in a greenhouse for ten days. The above-mentioned dilution solutions were sprayed to foliar parts so as to adhere adequately onto the surfaces of leaves of the above wheats. After spraying the dilutions, the plants were air-dried, and thereto an aqueous suspension of spores of wheat rust fungus (*Puccinia recondita*) spores was inoculated by spraying one day after the application. After the inoculation, the plants were placed at 23° C. under humid condition for one day, and are then cultivated at 23° C. under lighting for ten days, and a lesion area was examined (hereinafter referred to as "lesion area of the treated group").

Whereas, wheats were cultivated similarly to the treated group except that no foliage application of the above-mentioned agent solutions were done, and the wheat red rust fungus (*Puccinia recondita*) were inoculated, and the lesion area thereof was examined (hereinafter referred to as "lesion area of the untreated group").

From each of the lesion area of the treated group and the untreated group, respectively, the efficacy of the treated group was calculated by the below-mentioned Equation 2.

From the test results, it was acknowledged that a synergistic effect was shown in the mixed-use group of the present compound 1 and the present compound 2-1 when compared with the single-use group of each of the above-mentioned compounds.

$$\text{Efficacy (\%)} = [1 - (\text{lesion area of the treated group}) / (\text{lesion area of the untreated group})] \times 100 \quad \text{Equation 2}$$

TABLE 6

| Testing compound | Concentration in medium (ppm) | mixing ratio (Present compound 1:Present compound 2-1) | Efficacy (%) |
|---|---|---|---|
| Present compound 1 | 0.01 | — | 68 |
| Present compound 1 | 0.0005 | — | 56 |
| Present compound 2-1 | 0.005 | — | 51 |
| Present compound 2-1 | 0.001 | — | 44 |
| Present compound 1 + Present compound 2-1 | 0.01 + 0.001 | 1:0.1 | 100 |
| Present compound 1 + Present compound 2-1 | 0.0005 + 0.005 | 1:10 | 100 |

The invention claimed is:

1. A composition for controlling a plant disease comprising a synergistically effective amount of a carboxamide compound represented by a formula (1):

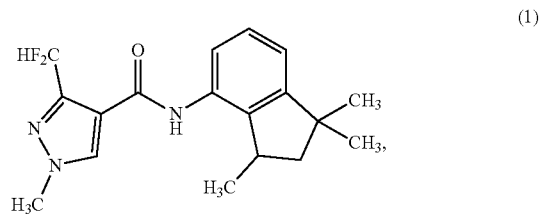

and an azole compound represented by a formula (2):

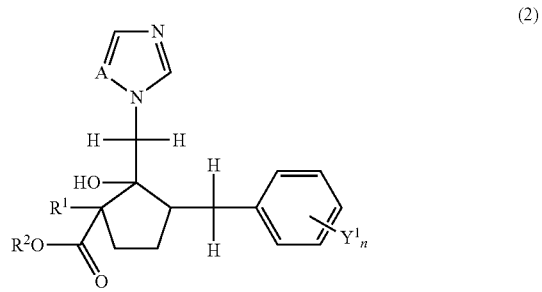

wherein $R^1$ represents a C1-C6 alkyl group, $R^2$ represents a hydrogen atom, a C1-C3 alkyl group, a C2-C3 alkenyl group, or a C2-C3 alkylnyl group, A represents a nitrogen atom, $Y^1$ represents a halogen atom, and n is 0 or 1.

2. The composition for controlling a plant disease according to claim 1 wherein the compound represented by the formula (2) represents a compound represented by a formula (2a):

(2a)

wherein
  Y² represents a chlorine atom, a fluorine atom or a hydrogen atom.

3. The composition for controlling a plant disease according to claim 2 wherein the compound represented by the formula (2a) is the compound wherein Y² represents a chlorine atom in the formula (2a).

4. The composition for controlling a plant described in claim 1 wherein a weight ratio of the compound represented by the formula (1) to the compound represented by the formula (2) is 1:0.0125 to 1:500.

5. A method for controlling a plant disease comprising applying each of a synergistically effective amount of a carboxamide compound represented by a formula (1):

(1)

and an azole compound represented by a formula (2):

(2)

wherein
  R¹ represents a C1-C6 alkyl group,
  R² represents a hydrogen atom, a C1-C3 alkyl group, a C2-C3 alkenyl group, or a C2-C3 alkylnyl group,
  A represents a nitrogen atom,
  Y¹ represents a halogen atom, and
  n is 0 or 1,
to a plant or a soil for cultivating the plant.

6. The method for controlling a plant disease according to claim 5 wherein the step of applying to a plant or a soil for cultivating the plant is a step of applying to a seed.

7. A synergistically effective combination of a carboxamide compound represented by a formula (1):

(1)

and an azole compound represented by a formula (2):

(2)

wherein
  R¹ represents a C1-C6 alkyl group,
  R² represents a hydrogen atom, a C1-C3 alkyl group, a C2-C3 alkenyl group, or a C2-C3 alkylnyl group,
  A represents a nitrogen atom,
  Y¹ represents a halogen atom, and
  n is 0 or 1.

* * * * *

UNITED STATES PATENT AND TRADEMARK OFFICE
CERTIFICATE OF CORRECTION

PATENT NO.        : 10,349,659 B2
APPLICATION NO.   : 15/748799
DATED             : July 16, 2019
INVENTOR(S)       : Dai Hirotomi et al.

Page 1 of 1

It is certified that error appears in the above-identified patent and that said Letters Patent is hereby corrected as shown below:

On the Title Page

Please remove the header and item (63) listed below:
"Related U.S. Application Data
(63) Continuation of application No. PCT/JP2016/073634, filed on Aug. 10, 2016."

Signed and Sealed this
Tenth Day of September, 2019

Andrei Iancu
*Director of the United States Patent and Trademark Office*